United States Patent
Baba et al.

[11] Patent Number: 5,811,058
[45] Date of Patent: Sep. 22, 1998

[54] HEAT-RESISTANT MAGNESIUM ALLOY

[75] Inventors: Tsuyoshi Baba; Kensuke Honma; Masao Ichikawa, all of Wako, Japan

[73] Assignee: Honda Giken Kogyo Kabushiki Kaisha, Tokyo, Japan

[21] Appl. No.: 805,436

[22] Filed: Feb. 25, 1997

[30] Foreign Application Priority Data

Feb. 27, 1996 [JP] Japan .................................. 8-039244
Jul. 30, 1996 [JP] Japan .................................. 8-216612

[51] Int. Cl.$^6$ .................................................. C22C 23/02
[52] U.S. Cl. ........................... 420/410; 148/406; 148/420
[58] Field of Search .................... 148/406, 420, 148/538; 420/408, 409, 410

[56] References Cited

U.S. PATENT DOCUMENTS 5,073,207  12/1991  Faure et al. ............................... 420/407
5,078,962  1/1992  Regazzoni et al. ...................... 420/402

FOREIGN PATENT DOCUMENTS

0419375A1  3/1991  European Pat. Off. .
2314262   1/1977  France .
6-25790   2/1994  Japan .
6-200348  7/1994  Japan .
7-011374  1/1995  Japan .
7-278717  10/1995  Japan .

OTHER PUBLICATIONS

Patent Abstracts of Japan, Publication No. JP07 278717 A, Publication Date Oct. 14, 1995.
Giesserei–Praxis, Oct. 1971, Berlin, pp. 355–366; Magnesium–Druckgusslegierungen, K. E. Nelson.

Primary Examiner—Margery Phipps
Attorney, Agent, or Firm—Birch, Stewart, Kolasch & Birch, LLP

[57] ABSTRACT

A heat-resistant magnesium alloy containing, based on the total weight of the alloy, 4.5–10 wt. % of aluminum, 0.1–3 wt. % of calcium, 1–3 wt. % of a rare earth element and 0.2–1 wt. % of manganese and having a composition that the contents of aluminum, calcium and the rare earth element satisfy the relationship of the following expression (1):

$$1.66 + 1.33\ Ca + 0.37\ RE \leq Al \leq 2.77 + 1.33\ Ca + 0.74\ RE$$

wherein Ca, RE and Al represent the weight percentages of Ca, at least one rare earth element and aluminum contained in the alloy, respectively, in the relationship.

5 Claims, 8 Drawing Sheets

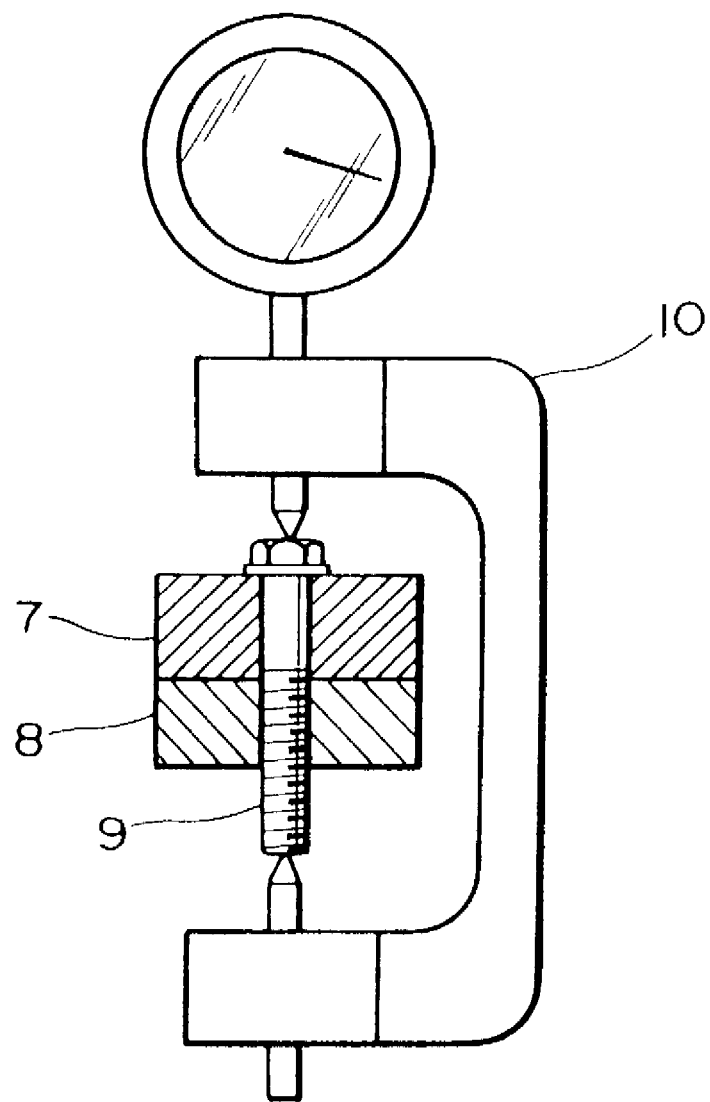

HEAT-RESISTANT MAGNESIUM ALLOY

BACKGROUND OF THE INVENTION

1. Field of the Invention

The present invention relates to a heat-resistant magnesium alloy suitable for use in mechanical parts of which weight saving is required, for example, automobile parts.

2. Description of the Background Art

In recent years, there has been a demand for weight saving of automobile parts with a view toward improving fuel consumption of automobiles. It has been investigate to use magnesium alloys as materials for such parts.

In the past, Mg—Al—Zn—Mn type alloys (AZ91D alloys) containing 9 wt. % of aluminum, 1 wt. % of zinc and 0.5 wt. % of manganese, Mg—Al—Mn type alloys (AM60B alloys) containing 6 wt. % of aluminum and 0.3 wt. % of manganese, and the like have been known. However, the strength of all the above-described magnesium alloys is reduced at about 120° C., and so they are unfit when used at a high-temperature strength or high heat resistance is required.

Mg—Al—RE (rare earth element) type alloys to which a rare earth element is added in order to improve the high-temperature strength of the above magnesium alloys, for example, an AE42 alloy (specification of Dow Chemical Co.) containing 4 wt. % of aluminum and 2 wt. % of a rare earth element, are known. However, the AE42 alloy is insufficient in creep strength and is hence unfit for uses of which high high-temperature strength is required in a pressed state.

Therefore, there have been proposed various attempts to improve material characteristics such as high-temperature strength and creep strength.

For example, Japanese Patent Application Laid-Open No. 25790/1994 discloses magnesium alloys containing 2–10 wt. % of aluminum, 1.4–10 wt. % of calcium, having a Ca/Al ratio of at least 0.7 and further containing each at most 2 wt. % of zinc, manganese, zirconium and silicon, and at most 4 wt. % of at least one element selected from rare earth elements (for example, yttrium, neodymium, lanthanum, cerium and Misch metals). This publication describes the fact that the inclusion of the rare earth element permits improvement in the high-temperature strength of the magnesium alloys, and this effect is further enhanced by using the rare earth element in combination with calcium.

Besides, Japanese Patent Application Laid-Open No. 11374/1995 discloses magnesium alloys containing 1.5–10 wt. % of aluminum, at most 2 wt. % of a rare earth element and 0.25–5.5 wt. % of calcium. According to the above magnesium alloys, creep strength at high temperature is said to be improved.

Further, Japanese Patent Application Laid-Open No. 278717/1995 discloses magnesium alloys containing 1.5–10 wt. % of aluminum, at most 2 wt. % of a rare earth element and 0.25–2.5 wt. % of calcium. According to the above magnesium alloys, resistance to thermal settling (percent reduction in axial force) is said to be improved.

However, when calcium is contained in a magnesium alloy, the resulting alloy involves a disadvantage that it tends to undergo casting crack, in particular, high-heat crack right after casting in the case of a casting process high in cooling rate, such as die casting.

SUMMERY OF THE INVENTION

It is an object of the present invention to provide a magnesium alloy which solves the above disadvantage, is excellent in high-temperature properties such as high-temperature strength and creep elongation and undergoes no casting crack.

Another object of the present invention is to provide a magnesium alloy produced by die casting and having excellent residual joint axial force under a high-temperature and high-load environment when joined by a bolt or bolts.

In a casting process high in cooling rate, it is considered that casting crack is caused when the strength of the resulting cast product is insufficient against stress generated with shrinkage upon solidification of the cast product.

The structure of a magnesium alloy is generally composed of a dendrite structure. A part of the dendrite may be converted into an α crystal grain by subsequent working, heat treatment and/or the like. However, it is difficult to distinguish the dendrite from the α crystal grain at a glance. Therefore, the matrix and grain boundary of the cast structure are described as "dendrite or α crystal grain" and "dendrite cell or α crystal grain boundary", respectively, in this specification.

When calcium and a rare earth element are contained in a magnesium alloy, a solid solution is scarcely formed because calcium and the rare earth element are low in solid solubility in the matrix of the magnesium alloy. Therefore, they are crystallized out as such a network-like eutectic phase as they fill up the space of the dendrite cell or α crystal grain boundary. It is known that the heat resistance of the magnesium alloy is improved by the eutectic phase. However, the magnesium alloy containing calcium and the rare earth element scarcely gains strength between matrices (dendrite or α crystal grains) until the eutectic phase solidifies. Therefore, it is considered that such a magnesium alloy does not gain resisting force against the stress generated upon the casting, and so it tends to undergo casting crack.

Thus, the present inventors have carried out a repeated investigation as to the compositions of magnesium alloys containing a rare earth element. As a result, it has been found that the reason why calcium and the rare earth element are crystallized out as the eutectic phase is that the amount of aluminum present in the grain boundary (dendrite cell or α crystal grain boundary) of the magnesium alloy is little, and the casting crack can hence be reduced by containing aluminum in the magnesium alloy in an amount appropriate to the contents of calcium and the rare earth element.

The present invention has been developed on the basis of the above finding.

According to an aspect of the present invention, there is thus provided a heat-resistant magnesium alloy containing, based on the total weight of the alloy, 4.5–10 wt. % of aluminum, 0.1–3 wt. % of calcium, 1–3 wt. % of a rare earth element and 0.2–1 wt. % of manganese and having a composition where the contents of aluminum, calcium and the rare earth element satisfy the relationship of the following expression (1):

$$1.66 + 1.33b + 0.37c \leq a \leq 2.77 + 1.33b + 0.74c \tag{1}$$

wherein a represents the content of aluminum, b represents the content of calcium, and c represents the content of the rare earth element.

In a magnesium alloy containing aluminum, aluminum is contained as a supersaturated solid solution in the matrix (dendrite cell or α crystal grain) of the magnesium alloy where its structure is formed by quenching. However, when the content of aluminum is further increased, aluminum is discharged in the grain boundary (dendrite cell or α crystal grain boundary). Since the above calcium and rare earth element are high in bonding property to aluminum, the structural form of the magnesium alloy is changed when the amount of aluminum in the grain boundary (dendrite cell or α crystal grain boundary) is increased, so that the calcium and rare earth element form a compound phase containing aluminum. Since the compound phase containing the above calcium and rare earth element, and aluminum solidifies at a temperature higher than such a network-like eutectic phase as the calcium and rare earth element fill up the space of the dendrite cell or α crystal grain boundary, the resulting magnesium alloy gains strength resistant to stress generated with shrinkage upon solidification of a cast product of the magnesium alloy.

Besides, the temperature of a liquid phase in a casting mold is lowered by increasing the amount of aluminum contained in the magnesium alloy. Therefore, the temperature range upon the solidification becomes narrow, so that stress generated with the shrinkage upon the solidification of the cast product of the magnesium alloy becomes weak.

According to the magnesium alloy of the above constitution, therefore, the casting crack can be reduced owing to the inclusion of aluminum in an amount within the above range to the contents of calcium and the rare earth metal.

On the other hand, when the amount of aluminum contained in a magnesium alloy becomes too great, a magnesium-aluminum compound ($Mg_{17}Al_{12}$) is deposed in its matrix and grain boundary. When the magnesium-aluminum compound undergoes coarse solidification in such a state, the alloy structure becomes thermally unstable, and so the resulting magnesium alloy incurs a possibility that its heat resistance may be lowered.

However, when the amount of aluminum contained in the magnesium alloy is controlled to an amount within the above range to the contents of calcium and the rare earth element, aluminum discharged in the grain boundary combines with the calcium and rare earth element, thereby preventing the deposition of the magnesium-aluminum compound. Besides, when manganese is contained in an amount within the above range in the magnesium alloy, the deposition of the magnesium-aluminum compound is prevented by manganese which is a peritectic system.

According to the magnesium alloy of the above constitution, therefore, heat resistance of the same degree as the prior art alloys can be obtained owing to the inclusion of aluminum and manganese in amounts within the above respective ranges to the contents of calcium and the rare earth element.

The heat-resistant magnesium alloy according to the present invention may be characterized in that it is used in die casting. In the die casting, cooling rate is high, and a casting material is constrained by a mold. Therefore, stress due to shrinkage upon solidification is liable to become great. According to the heat-resistant magnesium alloy of the present invention, the stress is however weakened as described above, and strength resistant to the stress can be obtained, so that casting crack upon die casting can be reduced.

The heat-resistant magnesium alloy according to the present invention may be characterized in that the rare earth element is contained as a Misch metal. As the rare earth element, there may be used one or more of scandium, yttrium, lanthanum, cerium, praseodymium, neodymium, promethium, samarium, europium, gadolinium, terbium, dysprosium, holmium, erbium, thulium, ytterbium and lutetium. However, it is expensive to isolate the rare earth element, so that the Misch metal, which is comparatively cheap, may be preferably used. Misch metals are natural alloys of a cerium group and contain cerium, lanthanum, praseodymium, neodymium, samarium and the like.

The present inventors have carried out a further investigation as to the heat-resistant magnesium alloy according to the first aspect of the present invention. As a result, it has been found that when the composition of the heat-resistant magnesium alloy, which falls within the above-described ranges, is further limited to a composition within specific ranges upon using it in die casting, the resulting alloy becomes a characteristic structural form and gains excellent residual joint axial force under a high-temperature and high-load environment when joined by a bolt or bolts.

The present invention has been led to completion on the basis of the above finding.

According to another aspect of the present invention, there is also provided a heat-resistant magnesium alloy obtained by die casting and containing an aluminum-calcium type compound which covers a dendrite or α crystal grain in an alloy structure, and an aluminum-rare earth element type compound in the form of a spherical particle, which is crystallized out in a dendrite cell or α crystal grain boundary.

According to the heat-resistant magnesium alloy according to the second aspect of the present invention, the composition of calcium, the rare earth element and aluminum contained in the alloy is limited to a composition within their specific ranges to subject it to die casting, whereby the aluminum-calcium type compound formed covers the whole surface of the dendrite or α crystal grain. The aluminum-calcium type compound is stable at a high temperature, and so the embrittlement of the cast structure can be prevented by covering the whole surface of the dendrite or α crystal grain with this compound.

Besides, according to the heat-resistant magnesium alloy according to the second aspect of the present invention, the aluminum-rare earth element type compound in the form of a spherical particle is crystallized out in the dendrite cell or α crystal grain boundary at the same time as the formation of the aluminum-calcium type compound. The aluminum-rare earth element type compound in the form of a spherical particle is crystallized out in a state that a wedge is driven into the aluminum-calcium type compound which covers the dendrite or α crystal grain, whereby the resistance to distortion at high temperature of the resulting alloy becomes very high.

As a result, the heat-resistant magnesium alloy according to the second aspect of the present invention can provide excellent residual joint axial force under a high-temperature and high-load environment when joined by a bolt or bolts.

Incidentally, to speak the truth, the aluminum-rare earth element type compound contains calcium. However, the content of the calcium is very low, and so such a compound is described as "aluminum-rare earth element type compound" in this specification.

The heat-resistant magnesium alloy of the above constitution can be obtained by die casting in a composition containing, based on the total weight of the alloy, 4.5–6.0 wt. % of aluminum, 1.2–2.2 wt. % of calcium and 1.0–3.0 wt. % of a rare earth element.

The heat-resistant magnesium alloy contains aluminum in the above range, whereby aluminum combines with the rare earth element and calcium to form an aluminum-calcium type compound which is an intermetallic compound.

Besides, the heat-resistant magnesium alloy contains the rare earth element in the above range, whereby the rare earth element forms an aluminum-rare earth element type compound in the form of a spherical particle.

Further, the heat-resistant magnesium alloy contains calcium in the above range, whereby the aluminum-rare earth element type compound is spheroidized, and moreover the aluminum-calcium type compound can cover the whole surface of the dendrite or α crystal grain.

Incidentally, the heat-resistant magnesium alloy may contain zinc in addition to aluminum, calcium and the rare earth element. However, when a compound phase containing zinc is formed in the grain boundary, the residual joint axial force of the resulting alloy is reduced, and so the content of zinc is within a range in which zinc may be contained as a solid solution in the matrix, and is 0.5 wt. % or lower.

Other objects, features and advantages of the present invention will be readily appreciated from the preferred embodiments of the present invention, which will be described subsequently in detail with reference to the accompanying drawings.

BRIEF DESCRIPTION OF THE DRAWINGS

FIG. 8 is an explanatory cross-sectional view illustrating how to measure an axial force;

DETAILED DESCRIPTION OF THE PREFERRED EMBODIMENTS

Figure 1:
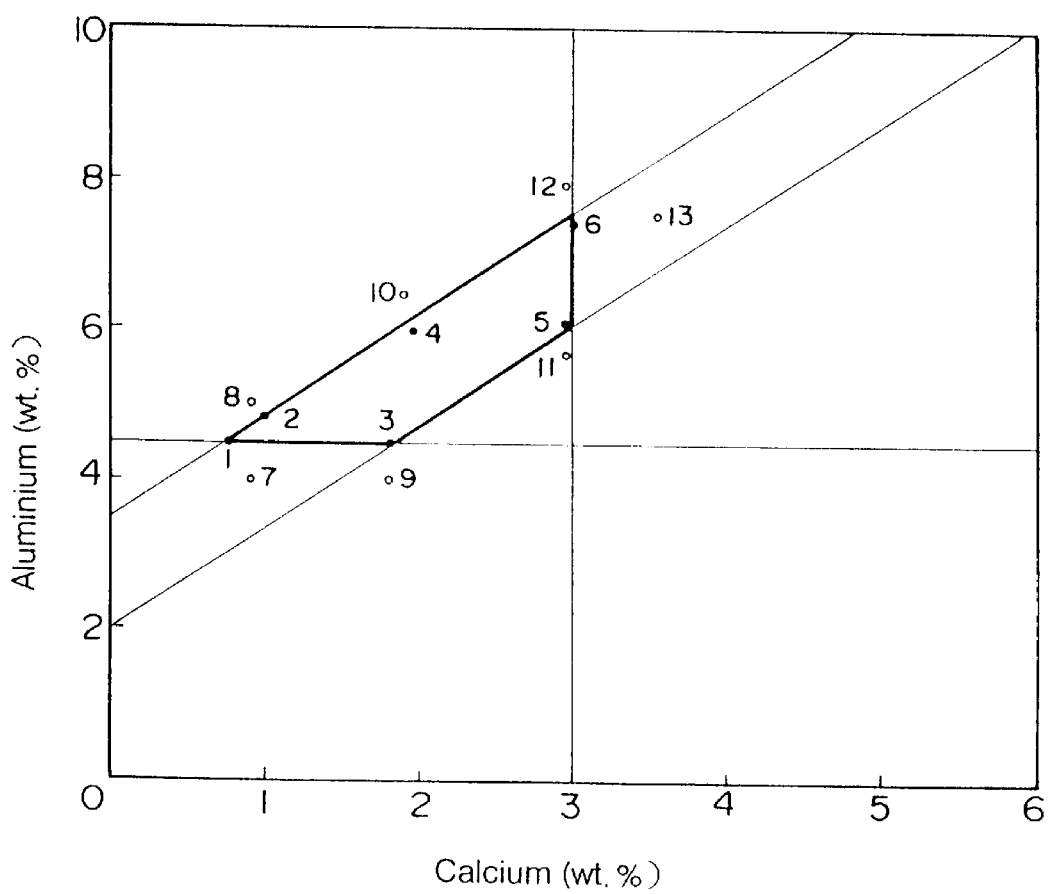
FIG. 1 is a graph illustrating a range of an aluminum content to a calcium content in a magnesium alloy according to the first aspect of the present invention where a content of the rare earth element is 1 wt. %.
Figure 2:
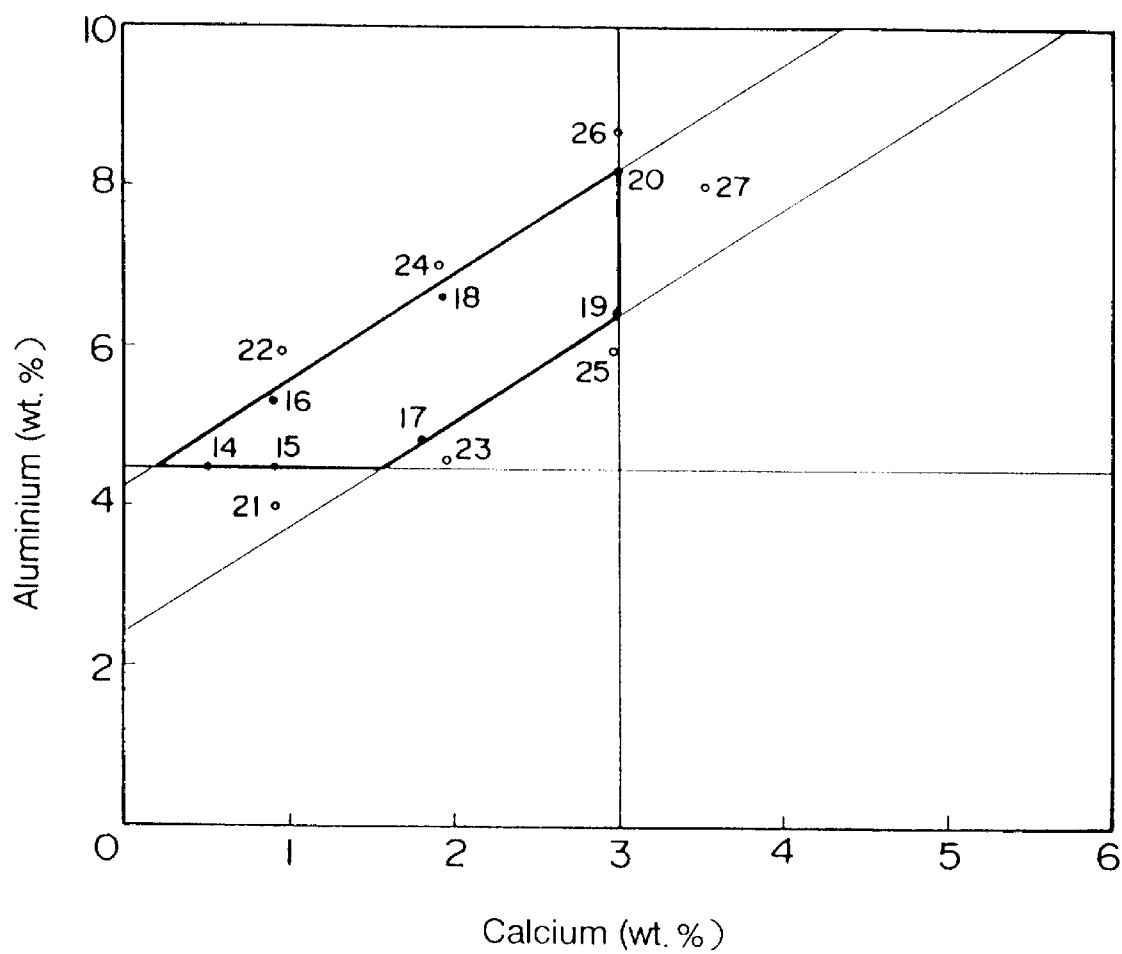
FIG. 2 is a graph illustrating a range of an aluminum content to a calcium content in a magnesium alloy according to the first aspect of the present invention where a content of the rare earth element is 2 wt. %.
Figure 3:
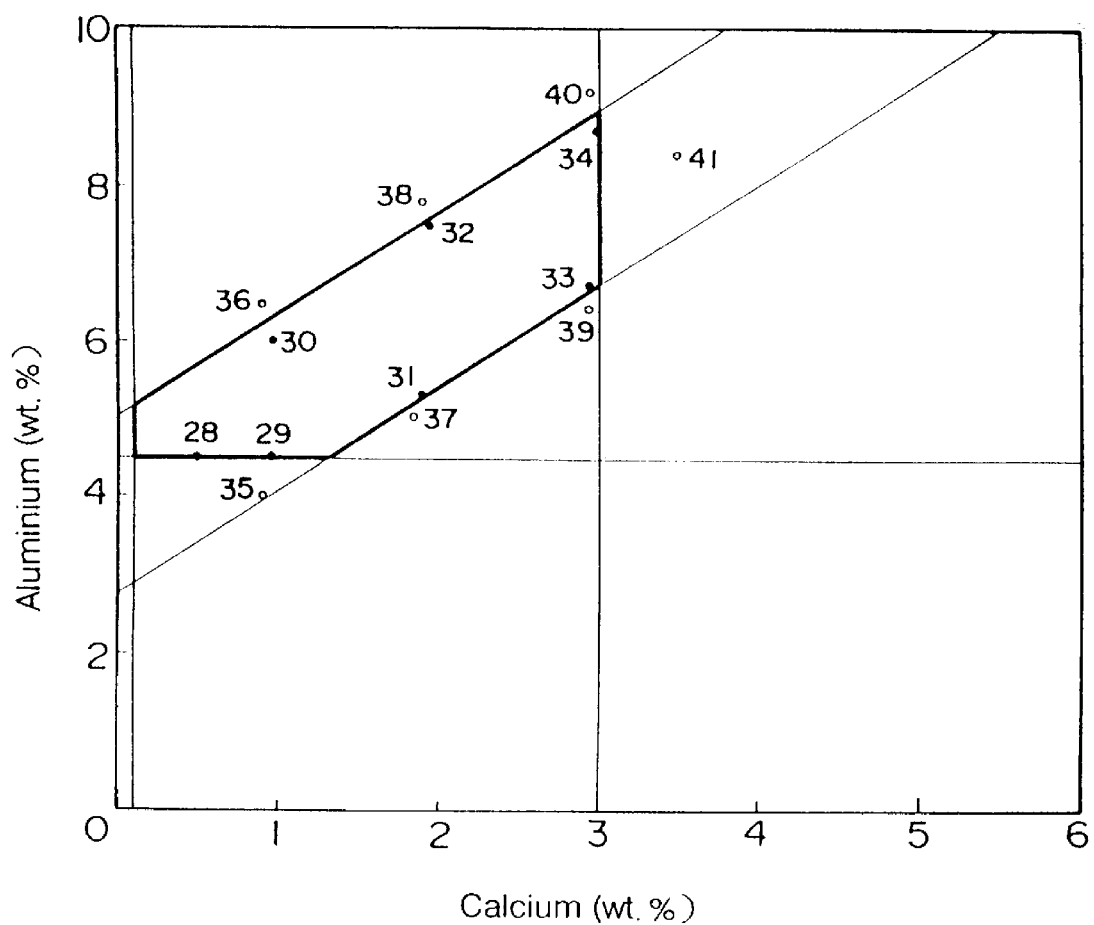
FIG. 3 is a graph illustrating a range of an aluminum content to a calcium content in a magnesium alloy according to the first aspect of the present invention where a content of the rare earth element is 3 wt. %.
Figure 4:
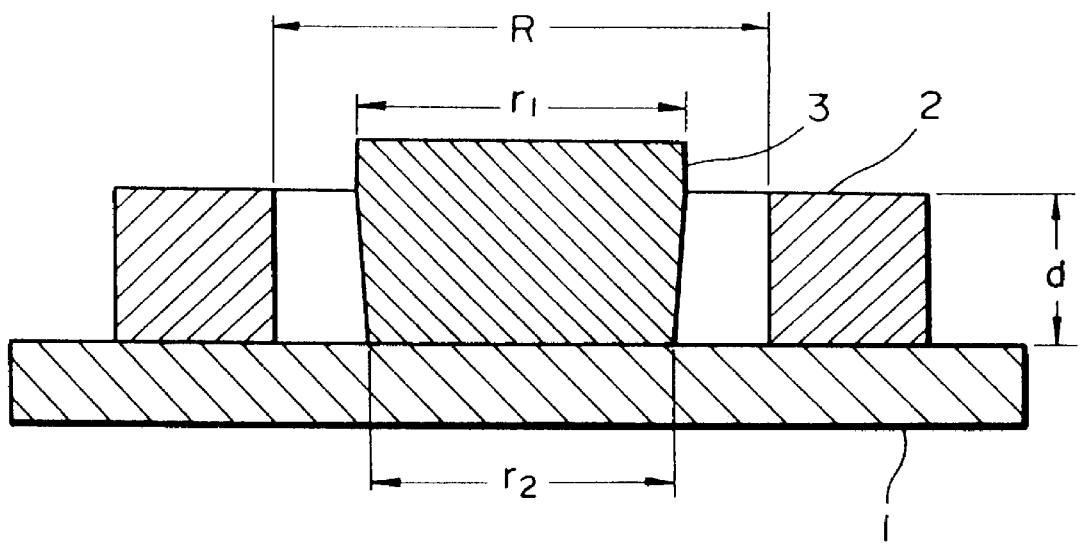
FIG. 4 is a cross-sectional view of a casting mold for a ring test used in determination of casting crack.

Embodiments of the present invention will hereinafter be described in more detail with reference to the accompanying drawings. FIGS. 1 to 3 are graphs each illustrating a range of an aluminum content to a calcium content in a magnesium alloy according to the first embodiment of the present invention where the content of the rare earth element is made constant. FIG. 4 is a cross-sectional view of a casting mold for ring test used in determination of casting crack.

Figure 5:
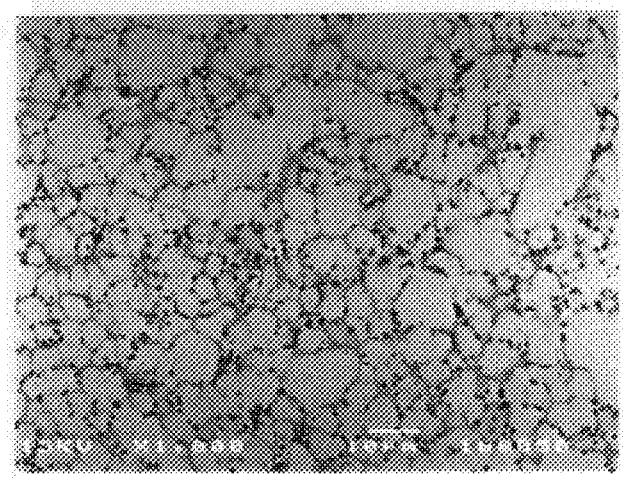
FIG. 5 is a copy of an electronic microphotograph illustrating a metallic structure of a magnesium alloy according to the second aspect of the present invention.
Figure 6:
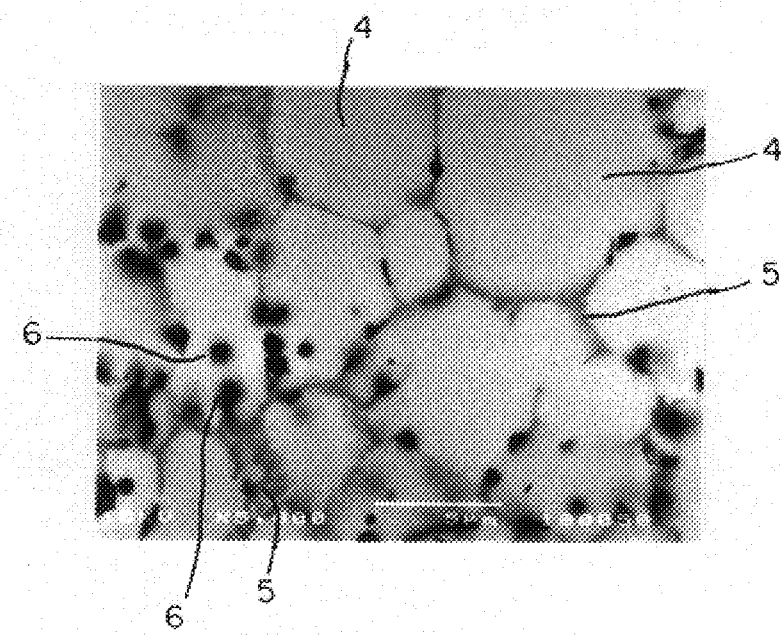
FIG. 6 is a copy of an electronic microphotograph illustrating the metallic structure of the magnesium alloy according to the second aspect of the present invention.
Figure 7:
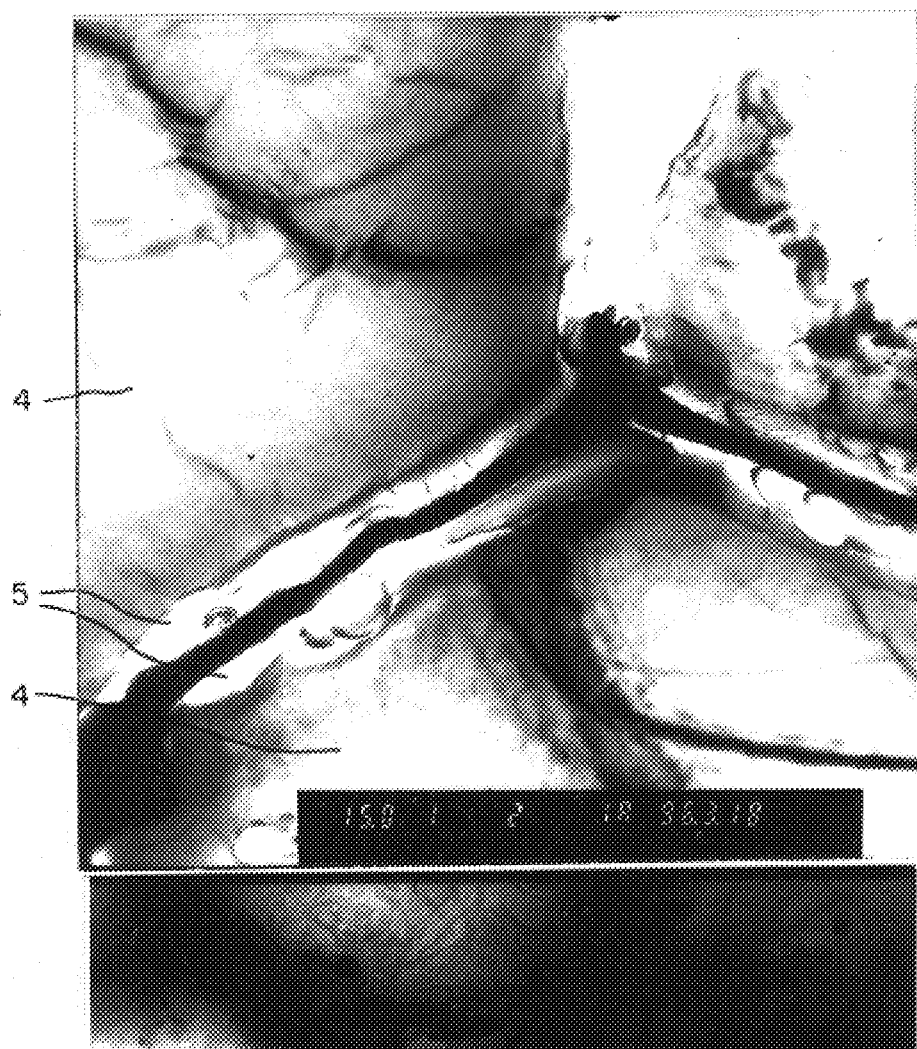
FIG. 7 is a copy of an electronic microphotograph illustrating the metallic structure of the magnesium alloy according to the second aspect of the present invention.

Besides, FIGS. 5 to 7 are copies of electronic microphotographs each illustrating a metallic structure of a magnesium alloy according to the second embodiment of the present invention, and FIG. 8 is an explanatory cross-sectional view illustrating how to measure a residual joint axial force of the magnesium alloy according to the second embodiment of the present invention when joined by a bolt.

Further, FIG. 9 to 13 are copies of electronic microphotographs each illustrating a metallic structure of a magnesium alloy according to a comparative example.

The magnesium alloys according to the first embodiment of the present invention will be first described.

The magnesium alloys according to this embodiment contain, based on the total weight of the alloy, 4.5–10 wt. % of aluminum, 0.1–3 wt. % of calcium, 1–3 wt. % of a Misch metal as a rare earth element and 0.2–1 wt. % of manganese and each have a composition that the contents of aluminum, calcium and the rare earth element satisfy the relationship of the following expression (1):

$$1.66+1.33b+0.37c \leq a \leq 2.77+1.33b+0.74c \quad (1)$$

wherein a represents the content of aluminum, b represents the content of calcium, and c represents the content of the rare earth element.

If the content of aluminum in the magnesium alloy is lower than 4.5 wt. % or the left member (1.66+1.33b+0.37c) of the expression (1), the effect of preventing the casting crack cannot be achieved. If the content of aluminum exceeds 10 wt. % or the right member (2.77+1.33b+0.74c) of the expression (1), the heat resistance, in particular, creep elongation of the resulting magnesium alloy is lowered.

If the content of calcium in the magnesium alloy is lower than 0.1 wt. %, the effect of preventing the casting crack cannot be achieved. If the content of calcium exceeds 3 wt. %, the strength and heat resistance, in particular, creep elongation of the resulting magnesium-alloy are lowered.

If the content of the rare earth element in the magnesium alloy is lower than 1 wt. %, the he at resistance, in particular, creep elongation of the resulting magnesium alloy is lowered. If the content of the rare earth element exceeds 3 wt. %, the effect of preventing the casting crack cannot be achieved.

If the content of manganese in the magnesium alloy is lower than 0.2 wt. %, the heat resistance, in particular, creep elongation of the resulting magnesium alloy is lowered. If the content of manganese exceeds 1 wt. %, the strength of the resulting magnesium alloy is lowered.

In this embodiment, as the Misch metal, that containing, for example, 23.7 wt. % of lanthanum, 58.0 wt. % of cerium, 4.7 wt. % of praseodymium, 12.6 wt. % of neodymium, less than 0.2 wt. % of samarium, less than 0.2 wt. % of iron, less than 0.3 wt. % of calcium and less than 0.1 wt. % of magnesium is used.

The magnesium alloys according to this embodiment are particularly suitable for uses of transmission cases, cases of engine parts and the like.

EXAMPLE 1

Magnesium alloys of Sample Nos. 1 to 6 were produced by including 1 wt. % of the Misch metal, 0.45 wt. % of manganese, and varied contents of aluminum and calcium.

In the magnesium alloys according to this example, the contents of aluminum and calcium were within ranges of 4.5–10 wt. % and 0.1–3 wt. %, respectively, and satisfied the relationship of the following expression (2):

$$2.03+1.33b \leq a \leq 3.51+1.33b \qquad (2)$$

wherein a represents the content of aluminum, and b represents the content of calcium.

Incidentally, the expression (2) corresponds to the expression (1) in which c is 1. In the magnesium alloys of Sample Nos. 1 to 6 according to this example, the contents of aluminum and calcium are in a region surrounded by a thick line in FIG. 1.

The magnesium alloys of Sample Nos. 1 to 6 were then used to conduct tests of casting crack and strength evaluation.

First, the casting crack test was performed by using a casting mold illustrated in FIG. 4 to cast a ring-like casting from each of the sample alloys, cooling the ring-like casting thus obtained and then measuring the lengths of cracks which occurred in the ring-like casting, whereby the casting crack was evaluated in terms of the total length of the cracks occurred.

As illustrated in FIG. 4, the ring-like casting is cast between an outer mold 2 and an inner mold 3 mounted on a base 1. The outer mold 2 is in the form of a ring having an inner diameter R of 58 mm and a thickness d of 19 mm, while the inner mold 3 is in the form of a disk which is tapered at its peripheral surface, has an upper external diameter $r_1$ of 38 mm and a lower external diameter $r_2$ of 37.6 and is thicker than the outer mold 2. Incidentally, ceramic powder was spray-coated and dried on the base 1 upon the casting of the ring-like casting.

Second, the test of strength evaluation was performed by using a 250-t cold chamber die casting machine to conduct die casting at a mold temperature of 100° C. and plunger speed of 1.7–2.5 m/sec, thereby producing a round bar having a diameter of about 20 mm and a length of 200 mm. A creep test piece and a tensile test piece, which had a threaded part having a grip section of outer diameter of 12 mm, a pitch of 1.0 mm and a 30 mm paralleled part of 8.0 mm in diameter, were machined from this round bar. The tensile test was performed at 150° C. and a crosshead speed of 0.5 m/sec. Besides, the creep test was performed under stress of 50 MPa at 150° C. to measure an elongation after 100 hours excluding an initial elongation.

The compositions of the magnesium alloys according to this example, and the results of the casting crack and strength evaluation tests are shown in the following Table 1.

COMPARATIVE EXAMPLE 1

Magnesium alloys of Sample Nos. 7 to 13 were produced in the same manner as in Example 1 except that 1 wt. % of the Misch metal and 0.45 wt. % of manganese were included, and contents of aluminum and calcium were varied outside the region surrounded by the thick line in FIG. 1, thereby performing the casting crack and strength evaluation tests in the same manner as in Example 1. The compositions of the magnesium alloys according to this comparative example, and the results of the casting crack and strength evaluation tests are shown in the following Table 1.

TABLE 1

| Sample | | Composition (wt. %) | | | | Casting crack length | Tensile strength | Elongation | Creep elongation |
|---|---|---|---|---|---|---|---|---|---|
| No. | | Ca | RE | Mn | Al | (mm) | (MPa) | (%) | (%) |
| Example 1 | 1 | 0.76 | 1.00 | 0.45 | 4.50 | 12 | 248 | 6.8 | 0.10 |
| | 2 | 0.90 | 1.02 | 0.45 | 4.70 | 0 | 248 | 6.5 | 0.10 |
| | 3 | 1.80 | 1.02 | 0.45 | 4.50 | 15 | 212 | 5.7 | 0.03 |
| | 4 | 1.96 | 1.00 | 0.45 | 5.96 | 0 | 239 | 4.9 | 0.06 |
| | 5 | 2.95 | 1.01 | 0.45 | 6.00 | 0 | 205 | 3.8 | 0.03 |
| | 6 | 3.00 | 1.00 | 0.46 | 7.40 | 0 | 238 | 3.1 | 0.10 |
| Comparative Example 1 | 7 | 0.90 | 1.00 | 0.45 | 3.98 | 61 | 232 | 6.5 | 0.01 |
| | 8 | 0.90 | 1.01 | 0.45 | 5.01 | 0 | 255 | 5.9 | 0.26 |
| | 9 | 1.80 | 1.01 | 0.45 | 4.00 | 62 | 200 | 5.1 | 0.01 |
| | 10 | 1.91 | 1.00 | 0.45 | 6.45 | 0 | 252 | 3.7 | 0.32 |
| | 11 | 2.95 | 1.00 | 0.45 | 5.65 | 62 | 196 | 2.6 | 0.01 |
| | 12 | 2.96 | 1.00 | 0.46 | 7.92 | 0 | 249 | 1.4 | 0.38 |
| | 13 | 3.55 | 1.00 | 0.45 | 7.53 | 0 | 169 | 0.7 | 0.01 |

RE: Rare earth element (Misch metal)

As apparent from Table 1, with respect to the magnesium alloys according to Example 1, the alloys of Sample Nos. 2, 4, 5 and 6 underwent no casting crack. Casting crack was observed on the alloys of Sample Nos. 1 and 3, but it was too slight to cause practical problems. In addition, the magnesium alloys according to Example 1 had excellent heat resistance as demonstrated by high tensile strength and low creep elongation at 150° C.

On the other hand, with respect to the magnesium alloys according to comparative Example 1, the alloys of Sample Nos. 7 and 9, whose aluminum content was lower than 4.5 wt. %, underwent casting crack. Besides, the alloy of Sample No. 11, whose aluminum and calcium contents were within ranges of 4.5–10 wt. % and 0.1–3 wt. %, respectively, but whose aluminum content was lower than the left member (2.03+1.33b) of the expression (2) (see FIG. 1), also underwent casting crack.

Further, the alloys of Sample Nos. 8, 10 and 12, whose aluminum and calcium contents were within ranges of 4.5–10 wt. % and 0.1–3 wt. %, respectively, but whose aluminum content was higher than the right member (3.51+1.33b) of the expression (2) (see FIG. 1), were apparently high in creep elongation and hence became low in heat resistance in a stressed state.

Furthermore, the alloy of Sample No. 13, whose calcium content exceeded 3 wt. %, was apparently too low in tensile strength to gain sufficient strength.

EXAMPLE 2

Magnesium alloys of Sample Nos. 14 to 20 were produced in the same manner as in Example 1 except that 2 wt. % of the Misch metal and 0.45 wt. % of manganese were included, and contents of aluminum and calcium were varied. In the magnesium alloys according to this example, the contents of aluminum and calcium were within ranges of 4.5–10 wt. % and 0.1–3 wt. %, respectively, and satisfied the relationship of the following expression (3):

$$2.40+1.33b \leq a \leq 4.25+1.33b \quad (3)$$

wherein a represents the content of aluminum, and b represents the content of calcium.

Incidentally, the expression (3) corresponds to the expression (1) in which c is 2. In the magnesium alloys of Sample Nos. 14 to 20 according to this example, the contents of aluminum and calcium are in a region surrounded by a thick line in FIG. 2.

The magnesium alloys of Sample Nos. 14 to 20 were then used to conduct tests of casting crack and strength evaluation in the same manner as in Example 1. The compositions of the magnesium alloys according to this example, and the results of the casting crack and strength evaluation tests are shown in the following Table 2.

COMPARATIVE EXAMPLE 2

Magnesium alloys of Sample Nos. 21 to 27 were produced in the same manner as in Example 1 except that 2 wt. % of the Misch metal and 0.45 wt. % of manganese were included, and contents of aluminum and calcium were varied outside the region surrounded by the thick line in FIG. 2, thereby performing the casting crack and strength evaluation tests in the same manner as in Example 1. The compositions of the magnesium alloys according to this comparative example, and the results of the casting crack and strength evaluation tests are shown in the following Table 2.

magnesium alloys according to Example 2 had excellent heat resistance as demonstrated by high tensile strength and low creep elongation at 150° C.

On the other hand, with respect to the magnesium alloys according to Comparative Example 2, the alloy of Sample No. 21, whose aluminum content was lower than 4.5 wt. %, underwent casting crack. Besides, the alloys of Sample Nos. 23 and 25, whose aluminum and calcium contents were within ranges of 4.5–10 wt. % and 0.1–3 wt. %, respectively, but whose aluminum content was lower than the left member (2.40+1.33b) of the expression (3) (see FIG. 2), also underwent casting crack.

Further, the alloys of Sample Nos. 22, 24 and 26, whose aluminum and calcium contents were within ranges of 4.5–10 wt. % and 0.1–3 wt. %, respectively, but whose aluminum content was higher than the right member (4.25+1.33b) of the expression (3) (see FIG. 2), were apparently high in creep elongation and hence became low in heat resistance in a stressed state.

Furthermore, the alloy of Sample No. 27, whose calcium content exceeded 3 wt. %, was apparently too low in tensile strength to gain sufficient strength.

EXAMPLE 3

Magnesium alloys of Sample Nos. 28 to 34 were produced in the same manner as in Example 1 except that 3 wt. % of the Misch metal and 0.45 wt. % of manganese were included, and the contents of aluminum and calcium were varied. In the magnesium alloys according to this example, the contents of aluminum and calcium were within ranges of 4.5–10 wt. % and 0.1–3 wt. %, respectively, and satisfied the relationship of the following expression (4):

$$2.77+1.33b \leq a \leq 4.99+1.33b \quad (4)$$

wherein a represents the content of aluminum, and b represents the content of calcium.

Incidentally, the expression (4) corresponds to the expression (1) in which c is 3. In the magnesium alloys of Sample

TABLE 2

| Sample | | Composition (wt. %) | | | | Casting crack length | Tensile strength | Elongation | Creep elongation |
|---|---|---|---|---|---|---|---|---|---|
| | No. | Ca | RE | Mn | Al | (mm) | (MPa) | (%) | (%) |
| Example 2 | 14 | 0.50 | 2.00 | 0.45 | 4.50 | 10 | 241 | 6.9 | 0.03 |
| | 15 | 0.90 | 2.00 | 0.45 | 4.50 | 12 | 226 | 6.5 | 0.03 |
| | 16 | 0.90 | 1.96 | 0.47 | 5.32 | 0 | 245 | 6.0 | 0.07 |
| | 17 | 1.81 | 2.00 | 0.45 | 4.85 | 0 | 202 | 5.4 | 0.03 |
| | 18 | 1.86 | 2.00 | 0.45 | 6.62 | 0 | 241 | 4.4 | 0.08 |
| | 19 | 2.99 | 1.96 | 0.45 | 6.47 | 0 | 196 | 3.4 | 0.03 |
| | 20 | 3.00 | 2.00 | 0.45 | 8.20 | 0 | 237 | 2.5 | 0.09 |
| Comparative | 21 | 0.90 | 2.00 | 0.45 | 4.00 | 57 | 215 | 6.3 | 0.01 |
| Example 2 | 22 | 0.95 | 2.00 | 0.45 | 5.95 | 0 | 258 | 5.2 | 0.35 |
| | 23 | 1.95 | 2.00 | 0.45 | 4.60 | 60 | 191 | 4.4 | 0.01 |
| | 24 | 1.91 | 2.00 | 0.45 | 7.00 | 0 | 248 | 3.2 | 0.20 |
| | 25 | 2.96 | 1.95 | 0.47 | 5.95 | 60 | 185 | 2.2 | 0.01 |
| | 26 | 2.99 | 2.00 | 0.46 | 8.70 | 0 | 248 | 1.5 | 0.37 |
| | 27 | 3.53 | 2.00 | 0.47 | 8.00 | 0 | 163 | 0.3 | 0.01 |

RE: Rare earth element (Misch metal)

As is apparent from Table 2, with respect to the magnesium alloys according to Example 2, the alloys of Sample Nos. 16 to 20 underwent no casting crack. Casting crack was observed on the alloys of Sample Nos. 14 and 15, but it was too slight to cause practical problems. In addition, the Nos. 28 to 34 according to this example, the contents of aluminum and calcium are in a region surrounded by a thick line in FIG. 3.

The magnesium alloys of Sample Nos. 28 to 34 were then used to conduct tests of casting crack and strength evaluation in the same manner as in Example 1. The compositions of the magnesium alloys according to this example, and the results of the casting crack and strength evaluation tests are shown in the following Table 3.

COMPARATIVE EXAMPLE 3

Magnesium alloys of Sample Nos. 35 to 41 were produced in the same manner as in Example 1 except that 3 wt. % of the Misch metal and 0.45 wt. % of manganese were included, and contents of aluminum and calcium were varied outside the region surrounded by the thick line in FIG. 3, thereby performing the casting crack and strength evaluation tests in the same manner as in Example 1. The compositions of the magnesium alloys according to this comparative example, and the results of the casting crack and strength evaluation tests are shown in the following Table 3.

Furthermore, the alloy of Sample No. 41, whose calcium content exceeded 3 wt. %, was apparently too low in tensile strength to gain sufficient strength.

EXAMPLE 4

Magnesium alloys of Sample Nos. 42 to 44 were produced in the same manner as in Example 1 except that the contents of the Misch metal, aluminum and calcium were 2 wt. %, 5 wt. % and 1.8 wt. %, respectively, and the content of manganese was varied within a range of 0.2–1.0 wt. %.

In the magnesium alloys according to this example, the contents of aluminum and calcium satisfied the relationship of the following expression (3):

$$2.40+1.33b \leq a \leq 4.25+1.33b \tag{3}$$

wherein a represents the content of aluminum, and b represents the content of calcium.

TABLE 3

| Sample | | Composition (wt. %) | | | | Casting crack length | Tensile strength | Elongation | Creep elongation |
|---|---|---|---|---|---|---|---|---|---|
| No. | | Ca | RE | Mn | Al | (mm) | (MPa) | (%) | (%) |
| Example 3 | 28 | 0.50 | 3.00 | 0.46 | 4.50 | 12 | 223 | 6.7 | 0.03 |
|  | 29 | 0.95 | 2.95 | 0.45 | 4.50 | 15 | 207 | 6.2 | 0.03 |
|  | 30 | 0.97 | 3.00 | 0.45 | 6.00 | 0 | 241 | 5.4 | 0.03 |
|  | 31 | 1.90 | 3.00 | 0.47 | 5.31 | 0 | 191 | 4.8 | 0.03 |
|  | 32 | 1.95 | 2.96 | 0.45 | 7.48 | 0 | 241 | 3.7 | 0.07 |
|  | 33 | 2.95 | 3.00 | 0.45 | 6.70 | 0 | 190 | 3.1 | 0.03 |
|  | 34 | 3.00 | 3.00 | 0.45 | 8.71 | 0 | 231 | 2.0 | 0.03 |
| Comparative | 35 | 0.91 | 2.95 | 0.45 | 4.00 | 59 | 196 | 6.0 | 0.01 |
| Example 3 | 36 | 0.90 | 3.00 | 0.45 | 6.45 | 0 | 254 | 4.8 | 0.24 |
|  | 37 | 1.85 | 2.97 | 0.46 | 5.00 | 58 | 186 | 4.1 | 0.03 |
|  | 38 | 1.90 | 3.00 | 0.45 | 7.90 | 0 | 252 | 2.6 | 0.31 |
|  | 39 | 2.95 | 3.00 | 0.45 | 6.39 | 60 | 178 | 1.8 | 0.03 |
|  | 40 | 2.96 | 3.00 | 0.45 | 9.20 | 0 | 244 | 1.4 | 0.25 |
|  | 41 | 3.50 | 3.00 | 0.45 | 8.22 | 0 | 161 | 0.3 | 0.03 |

RE: Rare earth element (Misch metal)

As is apparent from Table 3, with respect to the magnesium alloys according to Example 3, the alloys of Sample Nos. 30 to 34 underwent no casting crack. Casting crack was observed on the alloys of Sample Nos. 28 and 29, but it was too slight to cause practical problems. In addition, the magnesium alloys according to Example 3 had excellent heat resistance as demonstrated by high tensile strength and low creep elongation at 150° C.

On the other hand, with respect to the magnesium alloys according to Comparative Example 3, the alloy of Sample No. 35, whose aluminum content was lower than 4.5 wt. %, underwent casting crack. Besides, the alloys of Sample Nos. 37 and 39, whose aluminum and calcium contents were within ranges of 4.5–10 wt. % and 0.1–3 wt. %, respectively, but whose aluminum content was lower than the left member (2.77+1.33b) of the expression (4) (see FIG. 3), also underwent casting crack.

Further, the alloys of Sample Nos. 36, 38 and 40, whose aluminum and calcium contents were within ranges of 4.5–10 wt. % and 0.1–3 wt. %, respectively, but whose aluminum content was higher than the right member (4.99+1.33b) of the expression (4) (see FIG. 3), were apparently high in creep elongation and hence became low in heat resistance in a stressed state.

As described above, the expression (3) corresponds to the expression (1) in which c is 2.

The magnesium alloys of Sample Nos. 42 to 44 were then used to conduct tests of casting crack and strength evaluation in the same manner as in Example 1. The compositions of the magnesium alloys according to this example, and the results of the casting crack and strength evaluation tests are shown in the following Table 4.

COMPARATIVE EXAMPLE 4

Magnesium alloys of Sample Nos. 45 to 47 were produced in the same manner as in Example 1 except that the contents of the Misch metal, aluminum and calcium were 2 wt. %, 5 wt. % and 1.9 wt. %, respectively, and the content of manganese was varied outside a range of 0.2–1.0 wt. %, thereby performing the casting crack and strength evaluation tests in the same manner as in Example 1. The compositions of the magnesium alloys according to this comparative example, and the results of the casting crack and strength evaluation tests are shown in the following Table 4.

TABLE 4

| Sample | | Composition (wt. %) | | | | Casting crack length | Tensile strength | Elongation | Creep elongation |
|---|---|---|---|---|---|---|---|---|---|
| | No. | Ca | RE | Mn | Al | (mm) | (MPa) | (%) | (%) |
| Example 4 | 42 | 1.80 | 1.99 | 0.20 | 5.00 | 0 | 205 | 5.3 | 0.03 |
| | 43 | 1.81 | 2.00 | 0.70 | 5.05 | 0 | 205 | 5.3 | 0.02 |
| | 44 | 1.80 | 1.95 | 1.00 | 5.00 | 10 | 196 | 2.7 | 0.03 |
| Comp. | 45 | 0.90 | 1.99 | 0.00 | 5.00 | 0 | 201 | 4.3 | 0.17 |
| Ex. 4 | 46 | 0.91 | 2.00 | 0.10 | 5.05 | 0 | 202 | 4.2 | 0.16 |
| | 47 | 1.90 | 2.00 | 1.30 | 5.05 | 0 | 169 | 0.6 | 0.03 |

RE: Rare earth element (Misch metal)

As is apparent from Table 4, with respect to the magnesium alloys according to Example 4, whose manganese content was within the range of 0.2–1.0 wt. %, the alloys of Sample Nos. 42 and 43 underwent no casting crack. Casting crack was observed on the alloy of Sample No. 44, but it was too slight to cause practical problems. In addition, the magnesium alloys according to Example 4 had excellent heat resistance as demonstrated by high tensile strength and low creep elongation at 150° C.

On the other hand, with respect to the magnesium alloys according to Comparative Example 4, whose manganese content was outside the range of 0.2–1.0 wt. %, their casting crack was reduced like the magnesium alloys of Example 4. However, the alloy of Sample Nos. 45 and 46, whose manganese content was lower than 0.2 wt. %, showed creep elongation greater than that of the magnesium alloys according to Example 4. The magnesium alloy of Sample No. 47, whose manganese content was higher than 1.0 wt. %, was lower in tensile strength than that of the magnesium alloys of Example 4. It is hence apparent that these magnesium alloys are insufficient in heat resistance.

COMPARATIVE EXAMPLE 5

Magnesium alloys of Sample Nos. 48 to 50 were produced in the same manner as in Example 1 except that the content of manganese was controlled to 0.45 wt. %, the contents of calcium and aluminum were varied within ranges of 1.8–1.9 wt. % and 4.5–7.9, respectively, and the content of the Misch metal was varied outside a range of 1.0–3.0 wt., thereby performing the casting crack and strength evaluation tests in the same manner as in Example 1. The compositions of the magnesium alloys according to this comparative example, and the results of the casting crack and strength evaluation tests are shown in the following Table 5.

TABLE 5

| Sample | | Composition (wt. %) | | | | Casting crack length | Tensile strength | Elongation | Creep elongation |
|---|---|---|---|---|---|---|---|---|---|
| | No. | Ca | RE | Mn | Al | (mm) | (MPa) | (%) | (%) |
| Comp. Ex. 5 | 48 | 1.80 | 0.50 | 0.45 | 4.50 | 0 | 220 | 5.0 | 0.38 |
| | 49 | 1.90 | 4.00 | 0.45 | 7.90 | 28 | 234 | 2.4 | 0.01 |
| | 50 | 1.90 | 6.07 | 0.45 | 7.90 | 55 | 177 | 0.7 | 0.01 |

RE: Rare earth element (Misch metal)

As is apparent from Table 5, the alloy of Sample No. 48, in which the content of the Misch metal which was used as a rare earth element was lower than 1.0 wt. %, underwent no casting crack, but its creep elongation was great. Besides, the alloys of Sample Nos. 49 and 50, whose Misch metal content was higher than 3.0 wt. %, underwent casting crack.

The magnesium alloys according to the second embodiment of the present invention will hereinafter be described.

The magnesium alloys according to this embodiment can be obtained by die-casting alloy components in a composition containing, based on the total weight of the alloy, 4.5–6.0 wt. % of aluminum, 1.2–2.2 wt. % of calcium and 1.0–3.0 wt. % of a Misch metal as a rare earth element.

If the content of aluminum in the magnesium alloy is lower than 4.5 wt. %, the formation of the aluminum-calcium type compound and the aluminum-rare earth element type compound becomes insufficient, so that the magnesium-rare earth element type compound and magnesium-calcium type compound of the eutectic phase are lamellarly formed. On the other hand, if the content of aluminum exceeds 6.0 wt. %, excess aluminum which does not combine with the rare earth element or calcium turns into a crystalline phase, $\beta(Mg_{17}Al_{12})$, and the crystalline phase is thickly formed.

If the content of calcium is lower than 1.2 wt. %, the effect of spheroidizing the aluminum-rare earth element type compound cannot be achieved, and moreover the aluminum-calcium type compound cannot fully cover the whole surface of the dendrite or α crystal grain. On the other hand, if the content of calcium exceeds 2.2 wt. %, an eutectic phase is formed, resulting in a brittle magnesium alloy.

If the total content of the rare earth element in the magnesium alloy is lower than 1.0 wt. %, the absolute amount of the aluminum-rare earth element type compound crystallized out in the dendrite or α crystal grain is insufficient, so that the effect of improving residual joint axial force cannot be attained. On the other hand, if the content of the rare earth element exceeds 3.0 wt. %, an aluminum-rare earth element type compound, for example, in a compositional ratio of aluminum to the rare earth element of 2:1 coarsely precipitates primary compounds, resulting in a very brittle magnesium alloy.

The magnesium alloys according to this embodiment may contain manganese within a range of 0.2–1 wt. % based on the total weight of the alloy like the first embodiment.

Besides, the magnesium alloys according to this embodiment may also contain zinc within a range in which zinc may be contained as a solid solution in the matrix. Zinc is a solid solution-strengthening element like aluminum. However, zinc is easy to combine with rare earth elements and calcium, and so a zinc-rare earth element type compound, aluminum-zinc-rare earth element type compound, zinc-calcium type compound and aluminum-zinc-calcium type compound are formed. When such zinc-containing compounds are crystallized out in the grain boundary, the resulting alloy tends to reduce its residual joint axial force. Accordingly, the content of zinc in the magnesium alloys according to this embodiment, if contained, is within a range in which zinc may be contained as a solid solution in the matrix, and is 0.5 wt. % or lower.

In this embodiment, as the Misch metal, the same Misch metal as that used in the first embodiment is used.

In this embodiment, magnesium alloys containing an aluminum-calcium type compound which covers the whole surface of a dendrite or α crystal grain in an alloy structure, and an aluminum-rare earth element type compound in the form of a spherical particle, which is crystallized out in a dendrite cell or α crystal grain boundary, are obtained by conducting die casting in the above-described composition.

The results obtained by observing the structure of the magnesium alloy according to this embodiment will hereinafter be described taking the case of a magnesium alloy containing 5.0 wt. % of aluminum, 1.8 wt. % of calcium, 2.0 wt. % of the Misch metal as a rare earth element and 0.3 wt. % of manganese and obtained by die casting.

The structure of the magnesium alloy was observed by photographs of 1,000 and 5,000 magnifications of the alloy taken as a compositional image by a scanning electron microscope because it was difficult to separate the rare earth element type compounds from the calcium type compounds by an optical microscope. FIGS. 5 and 6 show copies of the electronic microphotographs of 1,000 and 5,000 magnifications, respectively.

In the structure of the magnesium alloy, it is apparent that as shown in FIG. 6, a lamellar aluminum-calcium type compound 5 which covers the whole surface of the dendrite or α crystal grain 4 is formed in a dendrite cell or α crystal grain boundary, and an aluminum-rare earth element type compound 6 in the form of a spherical particle ranging from 0.1 to 1 μm is further crystallized out in the compound 5.

A photograph of 75,000 magnifications was then obtained by a transmission electron microscope using a sample obtained by mechanically abrading and slicing the structure of the magnesium alloy, stamping a disc 3 mm across from the slice, abrading this disc up to #1,500 with wet abrasive paper and further abrading it into a thin film by electrolytic polishing. A copy of this electronic microphotograph is shown in FIG. 7.

In the structure of the magnesium alloy, it is apparent that as shown in FIG. 7, the lamellar aluminum-calcium type compound 5 which covers the dendrite or α crystal grain 4 in a thickness ranging from 0.1 to 1 μm is formed.

The compositions of the individual portions of the structure of the magnesium alloy shown in FIGS. 5 to 7 were then inferred by an energy dispersive method of X-ray spectroscopy. The results thereof are shown in the following Table 6. In the energy dispersive method of X-ray spectroscopy, cerium which amounts to about 60% of the Misch metal was detected as the rare earth element.

TABLE 6

|  | Mg | Al | Ca | RE |
| --- | --- | --- | --- | --- |
| Dendrite or α crystal grain boundary | — | 66.67 | 33.33 | — |
| Al—Ca type compound 5 (thin layer) | 21.13 | 51.51 | 26.55 | 0.81 |
| Al-RE type compound 6 (spherical particle) | — | 78.4 | 6.77 | 14.82 |

RE: Rare earth element (Misch metal)

It is apparent from Table 6 that the lamellar aluminum-calcium type compound 5 which covers the dendrite or α crystal grain 4 is composed mainly of aluminum and calcium. It is also apparent that the aluminum-rare earth element type compound 6 in the form of a spherical particle, which is crystallized out in the dendrite cell or α crystal grain boundary, is composed mainly of aluminum and the rare earth element and contains calcium.

In the energy dispersive method of X-ray spectroscopy, the reason why the aluminum-calcium type compound 5 contains magnesium is that magnesium in the matrix is unavoidably detected.

According to the magnesium alloys according to this embodiment, high resistance to distortion can be obtained under a high-temperature and high-load environment by the crystal structure of the above constitution. Therefore, excellent residual joint axial force can be obtained under the high-temperature and high-load environment when they are used in engine covers, case parts and the like and joined by bolts. Example of the magnesium alloys according to this embodiment and Comparative Example thereof will now be described.

EXAMPLE 5

In this example, magnesium having a purity of 99.9%, a Misch metal having a purity of 99.9% as a rare earth element, calcium having a purity of 99.8% and a magnesium alloy containing 3 wt. % of manganese were used to prepare compositions of Sample Nos. 51 to 60 by varying the contents of aluminum, the rare earth element, calcium, manganese and zinc within ranges of 4.5–6.0 wt. %, 1.0–3.0 wt. %, 1.2–2.2 wt. %, 0.2–1.0 wt. % and at most 0.5 wt. %, respectively, based on the total weight of the alloy. About 50 kg of an alloy material composed of each of the above compositions were cast into a thick plate of 50 mm×100 mm×15 mm in size by a 250-t cold chamber die casting machine.

The thick plates formed of the respective alloys of Sample Nos. 51 to 60 were then separately worked into two plates of 30 mm×30 mm×12 mm in size. A through-hole 6 mm across was made in one of them to provide a flange 7, while the other plate was subjected to thread cutting under conditions that a thread diameter was 6 mm and a pitch was 1.0 mm to provide a nut 8. The flange 7 and the nut 8 were joined by an M6 bolt 9 under a load of about 1,250 kgf (initial axial force).

After the flange 7 and the nut 8 which had been joined by the bolt 9 in the above-described manner were then subjected to a heat treatment for 400 hours in a muffle furnace of 150° C., they were taken out of the muffle furnace and air-cooled. An elongation of the bolt was then measured by a dial gauge 10 in a thermostatic chamber of 20° C., thereby calculating an axial force after 400 hours from a calibration curve prepared in advance. The axial force thus calculated was then compared with the initial axial force to calculate retention of axial force (%) in accordance with the following equation:

Retention of axial force (%)=(Axial force after 400 hours/Initial axial force)×100

Incidentally, the calibration curve was prepared by measuring the elongation of the bolt 9, by which the flange 7 and the nut 8 had been joined as described above, by the dial gauge 10 while applying a load to the bolt 9 by a 25-t autograph and plotting the elongation of the bolt versus the load. With respect to the respective alloys of Sample Nos. 51 to 60, their compositions and retention of axial force are shown in the following Table 7.

COMPARATIVE EXAMPLE 6

Thick plates of magnesium alloys composed separately of compositions of Sample Nos. 61 and 62 were die-cast in exactly the same manner as in Example 5 except that the content of aluminum was changed outside the range of 4.5–6.0 wt. % based on the total weight of the alloy.

Thick plates of magnesium alloys composed separately of compositions of Sample Nos. 63 and 64 were die-cast in exactly the same manner as in Example 5 except that the content of the rare earth element was changed outside the range of 1.0–3.0 wt. % based on the total weight of the alloy.

Thick plates of magnesium alloys composed separately of compositions of Sample Nos. 65 and 66 were die-cast in exactly the same manner as in Example 5 except that the content of calcium was changed outside the range of 1.2–2.2 wt. % based on the total weight of the alloy.

A thick plate of a magnesium alloy composed of a composition of Sample No. 67 was die-cast in exactly the same manner as in Example 5 except that the content of zinc was changed to an amount more than 0.5 wt. % based on the total weight of the alloy.

With respect to the respective alloys of Sample Nos. 61 to 67, their retention of axial force (%) was calculated in exactly the same manner as in Example 5. The compositions and retention of axial force of the alloys of Sample Nos. 61 to 67 are shown in the following Table 7.

TABLE 7

| Sample No. | Composition (wt. %) | | | | | Retention of axial force (%) |
|---|---|---|---|---|---|---|
| | Al | RE | Ca | Mn | Zn | |
| Example 5 | | | | | | |
| 51 | 4.50 | 1.01 | 1.20 | 0.30 | — | 65 |
| 52 | 5.35 | 1.05 | 1.92 | 0.29 | — | 67 |
| 53 | 5.95 | 1.02 | 2.20 | 0.32 | — | 67 |
| 54 | 4.50 | 1.96 | 1.20 | 0.30 | — | 68 |
| 55 | 5.55 | 1.95 | 1.71 | 0.28 | — | 70 |
| 56 | 5.98 | 1.93 | 2.16 | 0.31 | — | 70 |
| 57 | 4.50 | 2.95 | 1.20 | 0.27 | — | 68 |
| 58 | 5.59 | 2.99 | 1.71 | 0.30 | — | 70 |
| 59 | 6.00 | 2.96 | 2.20 | 0.30 | — | 70 |
| 60 | 5.53 | 2.01 | 1.70 | 0.33 | 0.5 | 65 |

TABLE 7-continued

| Sample No. | Composition (wt. %) | | | | | Retention of axial force (%) |
|---|---|---|---|---|---|---|
| | Al | RE | Ca | Mn | Zn | |
| Comparative Example 6 | | | | | | |
| 61 | 3.95 | 1.98 | 1.72 | 0.28 | — | — |
| 62 | 6.65 | 1.95 | 1.75 | 0.30 | — | 42 |
| 63 | 4.50 | 0.50 | 1.80 | 0.27 | — | 35 |
| 64 | 5.55 | 4.52 | 1.70 | 0.29 | — | — |
| 65 | 5.52 | 1.95 | 0.65 | 0.33 | — | 38 |
| 66 | 5.50 | 1.95 | 2.79 | 0.30 | — | — |
| 67 | 5.50 | 2.02 | 1.80 | 0.30 | 1.2 | 27 |

RE: Rare earth element (Misch metal)

It is apparent from Table 7 that all the magnesium alloys according to Example 5 have retention of axial force ranging from 65 to 70% and hence possess substantially the same excellent residual joint axial force as an aluminum alloy ADC12 under the high-temperature and high-load environment. On the other hand, all the magnesium alloys of Comparative Example 6, whose aluminum, rare earth element, calcium or zinc content is outside the range according to the present invention, had retention of axial force as low as at most 42%. In addition, the alloys of Sample Nos. 61, 64 and 66 were cracked under the high-temperature and high-load environment, and so their retention of axial force was unmeasurable.

The structures of the magnesium alloys of Sample Nos. 61 and 65 were observed. The results thereof will now be described.

Figure 9:
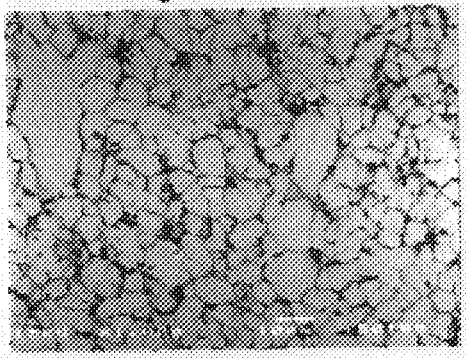
FIG. 9 is a copy of an electronic microphotograph illustrating a metallic structure of a magnesium alloy according to comparative Example 6.
Figure 10:
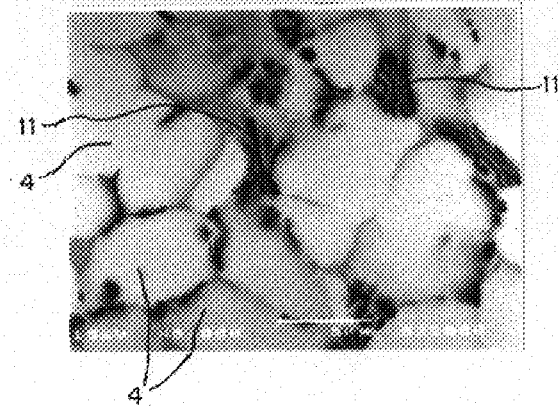
FIG. 10 is a copy of an electronic microphotograph illustrating the metallic structure of the magnesium alloy according to Comparative Example 6.

The structure of the magnesium alloy of Sample No. 61 was first observed by photographs of 1,000 and 5,000 magnifications of the alloy taken as a compositional image by a scanning electron microscope. FIGS. 9 and 10 show copies of the electronic microphotographs of 1,000 and 5,000 magnifications, respectively.

In the structure of the magnesium alloy, it is apparent that as shown in FIG. 10, many eutectics 11 are crystallized out in a dendrite cell or α crystal grain boundary, which is a grain boundary of the dendrite or α crystal grain 4, due to the low content of aluminum.

Figure 11:
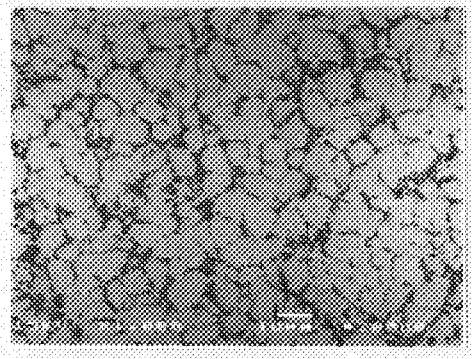
FIG. 11 is a copy of an electronic microphotograph illustrating a metallic structure of another magnesium alloy according to Comparative Example 6.
Figure 12:
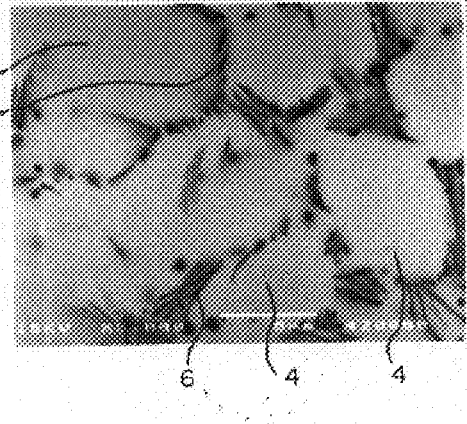
FIG. 12 is a copy of an electronic microphotograph illustrating the metallic structure of the another magnesium alloy according to Comparative Example 6.

The structure of the magnesium alloy of Sample No. 65 was then observed by photographs of 1,000 and 5,000 magnifications of the alloy taken as a compositional image by the scanning electron microscope. FIGS. 11 and 12 show copies of the electronic microphotographs of 1,000 and 5,000 magnifications, respectively.

In the structure of the magnesium alloy, it is apparent that as shown in FIG. 12, the aluminum-rare earth element type compound 6 crystallized out in a dendrite cell or α crystal grain boundary, which is a grain boundary of the dendrite or α crystal grain 4, is not spheroidized due to the low content of calcium.

A photograph of 75,000 magnifications was then obtained by a transmission electron microscope using a sample obtained by mechanically abrading and slicing the structure of the magnesium alloy, stamping a disc 3 mm across from the slice, abrading this disc up to #1,500 with wet abrasive paper and further abrading it into a thin film by electrolytic polishing. A copy of this electronic microphotograph is shown in FIG. 13.

Figure 13:
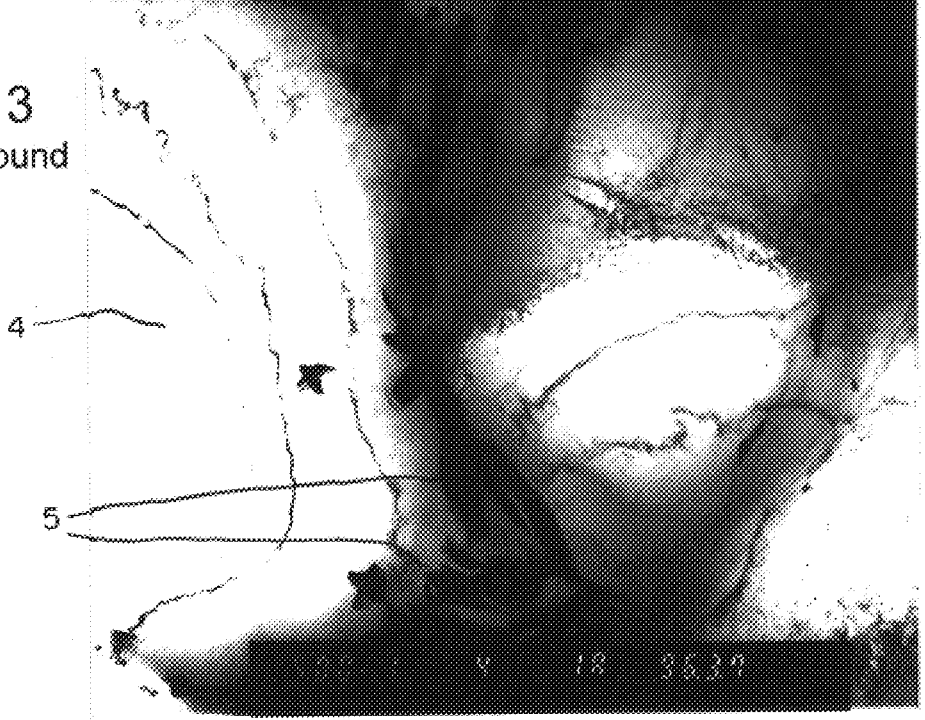
FIG. 13 is a copy of an electronic microphotograph illustrating the metallic structure of the another magnesium alloy according to Comparative Example 6.

In the structure of the magnesium alloy, it is apparent that as shown in FIG. 13, the lamellar aluminum-calcium type compound 5 incompletely covers the dendrite or α crystal grain 4 due to the low content of calcium.

What is claimed is:

1. A heat resistant magnesium alloy consisting essentially of, by weight, 4.5–10% aluminum, 0.1–3% calcium, 1–3% of at least one rare earth element, 0.2–1% manganese and the balance magnesium, wherein the alloy satisfies the relationship of:

$$1.66+1.33\ Ca+0.37\ RE \leq Al \leq 2.77+1.33\ Ca+0.74\ RE,$$

and wherein Ca, RE, and Al represent the weight percentage of Ca, at least one rare earth element, and aluminum contained in said alloy, respectively, in said relationship.

2. The heat-resistant magnesium alloy according to claim 1, which is suitable for use in die casting.

3. A heat-resistant magnesium alloy according to claim 2, which has been produced by die casting, and which contains a matrix phase which comprises a dendrite cell or an α crystal grain, wherein said dendrite cell or said α crystal grain is enveloped in an aluminum-calcium compound, and wherein said dendrite cell or said α crystal grain contains at least one precipitate of an aluminum-rare earth element compound, and said at least one precipitate is in the form of a spherical particle.

4. The heat-resistant magnesium alloy according to claim 2, which has been produced by die casting a composition containing, based on the total weight of the alloy, 4.5–6.0 wt. % of aluminum, 1.2.–2.2 wt. % of calcium and 1.0–3.0 wt. % of said at least one rare earth element.

5. The heat-resistant magnesium alloy according to claim 1, wherein said at least one rare earth element is a misch metal.

* * * * *